(12) United States Patent
Brenner et al.

(10) Patent No.: US 9,320,485 B2
(45) Date of Patent: Apr. 26, 2016

(54) SYSTEM AND METHOD FOR MOLECULAR BREAST IMAGING

(71) Applicant: GENERAL ELECTRIC COMPANY, Schenectady, NY (US)

(72) Inventors: Reuven Brenner, Tirat Carmel (IL); Osnat Zak, Tirat Carmel (IL); Avi Bar-Shalev, Tirat Carmel (IL); Nurit Rivka Warski, Tirat Carmel (IL)

(73) Assignee: GE MEDICAL SYSTEMS ISRAEL, LTD, Tel Aviv (IL)

( * ) Notice: Subject to any disclaimer, the term of this patent is extended or adjusted under 35 U.S.C. 154(b) by 61 days.

(21) Appl. No.: 13/954,120

(22) Filed: Jul. 30, 2013

(65) Prior Publication Data

US 2015/0036911 A1    Feb. 5, 2015

(51) Int. Cl.
*A61B 6/00* (2006.01)
*A61B 6/03* (2006.01)
*G06T 7/20* (2006.01)

(52) U.S. Cl.
CPC .............. *A61B 6/502* (2013.01); *A61B 6/037* (2013.01); *A61B 6/5264* (2013.01); *G06T 7/204* (2013.01); *G06T 2207/10128* (2013.01); *G06T 2207/30068* (2013.01)

(58) Field of Classification Search
None
See application file for complete search history.

(56) References Cited

U.S. PATENT DOCUMENTS

| | | | |
|---|---|---|---|
| 5,946,425 A * | 8/1999 | Bove, Jr. ............... | G06T 7/0026 382/128 |
| 7,177,953 B1 | 2/2007 | Jackson et al. | |
| 7,756,310 B2 * | 7/2010 | Manjeshwar ............ | G06K 9/00 348/441 |
| 7,783,096 B2 * | 8/2010 | Chen ....................... | A61B 6/00 382/128 |
| 7,953,265 B2 | 5/2011 | Sirohey et al. | |
| 2001/0038707 A1 * | 11/2001 | Ohara .................. | A61B 6/4233 382/132 |
| 2010/0008559 A1 * | 1/2010 | Borghese .............. | G06T 11/006 382/132 |
| 2010/0104505 A1 * | 4/2010 | O'Connor ............ | A61B 6/0414 424/1.11 |
| 2010/0119032 A1 * | 5/2010 | Yan ....................... | A61N 5/1049 378/4 |
| 2010/0135544 A1 * | 6/2010 | Mattiuzzi .............. | G06T 7/0028 382/128 |
| 2010/0290693 A1 * | 11/2010 | Cohen .................... | A61B 6/469 382/134 |
| 2011/0176710 A1 * | 7/2011 | Mattiuzzi .............. | G06F 19/321 382/128 |
| 2011/0249880 A1 * | 10/2011 | Parikh ...................... | A61B 5/06 382/131 |
| 2011/0275933 A1 * | 11/2011 | Dey ........................ | A61B 6/037 600/428 |
| 2013/0216113 A1 * | 8/2013 | O'Connor .............. | A61B 6/482 382/128 |

* cited by examiner

*Primary Examiner* — Matthew Bella
*Assistant Examiner* — Soo Shin
(74) *Attorney, Agent, or Firm* — Dean D. Small; The Small Patent Law Group, LLC (57) ABSTRACT

A method for motion correcting molecular breast imaging (MBI) images includes obtaining a plurality of two-dimensional (2D) images of a breast using a MBI system, selecting a reference image from the plurality of 2D images, selecting a feature of interest in the reference image, determining a location of the feature of interest in the reference image, calculating a correction value based on a difference in the location of the feature of interest in the reference image and a location of the feature of interest in a plurality of non-reference images, and aligning the non-reference 2D images with the reference image based on the calculated correction value.

20 Claims, 4 Drawing Sheets

SYSTEM AND METHOD FOR MOLECULAR BREAST IMAGING

BACKGROUND OF THE INVENTION

The subject matter disclosed herein relates generally to systems and methods for diagnostic medical imaging, and more particularly to Molecular Breast Imaging (MBI) systems.

Molecular Breast Imaging (MBI) is used to image breasts to detect, for example, tumors, lesions, and/or cancer. In operation, a patient is positioned within the MBI system such that the patient's breast is positioned between a pair of detectors. A single or a plurality of two-dimensional (2D) images, commonly each at a different orientation in respect to the patient's breast, is then acquired.

In operation, patient organ and lesion motion may be a significant source of image quality degradation. Respiratory motion is the most common involuntary motion encountered in MBI imaging due to the required duration of MBI scanning necessary to obtain clinically useful information. More specifically, in some cases the patient may move involuntarily such that the position of the breast is not consistent during the acquisition of each of the images. For example, in contrast to mammography imaging, where the breast is compressed for a short duration it takes to complete the X-ray exposure, MBI imaging generally performs data acquisition for several minutes. In some cases, a patient may experience discomfort due to the duration of the MBI imaging scan. Therefore, for MBI imaging the breast is immobilized between the MBI detectors using reduced pressure in comparison to the pressure used in mammography imaging. The reduced pressure is less effective in holding the breast in a fixed position and may therefore allow some motion of the breast respective to the MBI detectors. The combination of the reduced pressure and long imaging time may therefore increase the likelihood of image blurring due to motion. The involuntary motion may be particularly detrimental when a physician is determining the size of a lesion, determining the location of the lesion, or quantifying the lesion.

BRIEF DESCRIPTION OF THE INVENTION

In accordance with various embodiments, a method for motion correcting molecular breast imaging (MBI) images is provided. The method includes obtaining a plurality of two-dimensional (2D) images of a breast using a MBI system, selecting a reference image from the plurality of 2D images, selecting a feature of interest in the reference image, determining a location of the feature of interest in the reference image, calculating a correction value based on a difference in the location of the feature of interest in the reference image and a location of the feature of interest in a plurality of non-reference images, and aligning the non-reference images with the reference image based on the calculated correction value.

In accordance with other various embodiments, a molecular breast imaging (MBI) system is provided. The MBI system includes at least one detector having a plurality of pixels and a processing unit coupled to the detector. The processing unit is configured to obtain a plurality of two-dimensional (2D) images of a breast using a MBI system, receive a user input selecting a reference image from the plurality of 2D images, receive a user input selecting a feature of interest in the reference image, determine a location of the feature of interest in the reference image, calculate a correction value for each of a plurality of non-reference images based on a difference in a location of the feature of interest in the reference image and a location of the feature of interest in each of the non-reference images, and combine the non-reference images with the reference image based on the calculated correction values.

In a further embodiment, a non-transitory computer readable medium is provided. The non-transitory computer readable medium is encoded with a program to instruct a processing unit to obtain a plurality of two-dimensional (2D) images of a breast using a MBI system, receive a user input selecting a reference image from the plurality of 2D images, receive a user input selecting a feature of interest in the reference image, determine a location of the feature of interest in the reference image, calculate a correction value for each of a plurality of non-reference images based on a difference in a location of the feature of interest in the reference image and a location of the feature of interest in each of the non-reference 2D images, and combine the non-reference images with the reference image based on the calculated correction values.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a method for motion correcting images acquired using a Nuclear Medicine (NM) imaging system. For example, various embodiments provide a Molecular Breast Imaging (MBI) system and a method to acquire temporal imaging data of a patient's breast. Temporal as used herein means that the imaging data is time stamped such that a location of an event detected by the detectors may be associated with a time when the event was detected by the detectors. The temporal imaging data may be acquired in real-time while the MBI system is performing a dynamic scan of the breast. Optionally, the temporal emission data may be acquired after the breast is scanned. For example, the temporal emission data may be stored as list mode data. The temporal emission data may then be utilized to detect patterns in the images and also track variations of the movement over time. More specifically, the movement of a feature of interest may be measured to generate a correction value that is applied to the various images and/or list mode data acquired using the MBI system.

Figure 1:
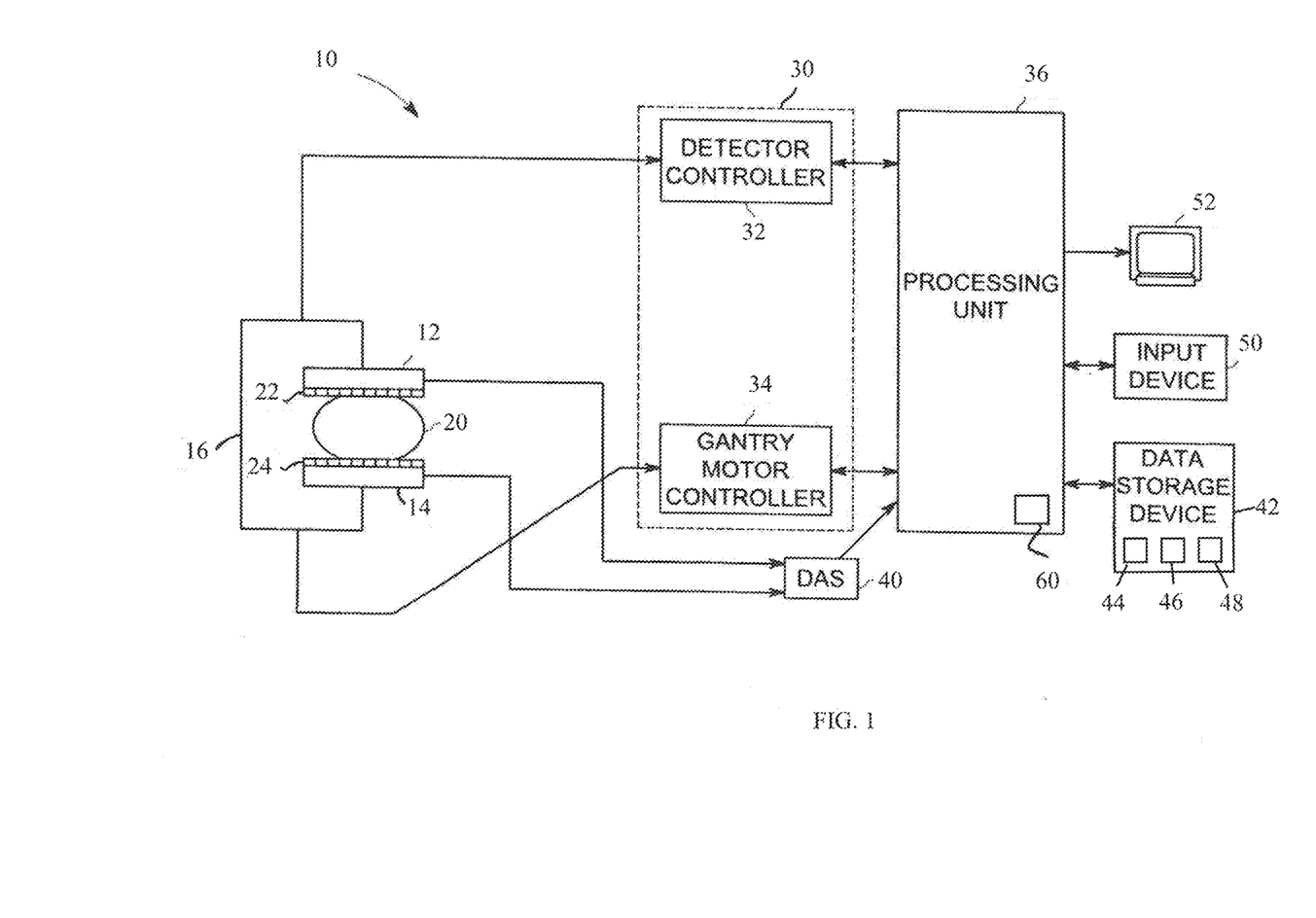
FIG. 1 a block diagram of an exemplary nuclear medicine imaging system embodied as a Molecular Breast Imaging (MBI) system constructed in accordance with various embodiments.

In various embodiments, the methods described herein may be implemented using an exemplary MBI system 10 shown in FIG. 1. The MBI system 10 includes imaging detectors 12 and 14 mounted on or to a gantry 16. Each detector 12 and 14 generally captures a two-dimensional (2D) image that may be defined by the x and y location of the pixel and the detector number. Moreover, in various embodiments, the 2D image captured by the detector 12 is obtained from a view that is approximately 180 degrees away from the 2D image captured by the detector 14. Further, in other exemplary embodiments, at least one of the detectors 12 and 14 may change orientation relative to the stationary or movable gantry 16. The detectors 12 and 14 may be registered such that features appearing at a given location in one detector may be correctly located and the data correlated in the other detector. Accordingly, in various embodiments common features in the two images acquired by the imaging detectors 12 and 14 may be combined.

Each of the detectors 12 and 14 has a radiation detection face (not shown) that is directed towards a structure of interest, for example, a breast 20 there between that may have a lesion. A pair of collimators 22 and 24 may be provided in combination or connection with the detectors 12 and 14, respectively. In various embodiments, the radiation detection faces of the detectors 12 and 14 are covered by the collimators 22 and 24. In some embodiments, the collimators 22 and 24 are registered parallel holes collimators coupled to the detection faces of the detectors 12 and 14.

For example, the detectors 12 and 14 may include collimators 22 and 24, respectively, provided directly on the surface of the detectors 12 and 14 and illustrated as parallel hole collimators. The detectors 12 and 14 are also capable of being rotated to some angle to provide various images of the breast 20 while remaining substantially parallel to each other. More specifically, the detector pair 12 and 1 generally remain in a parallel configuration, and the detector pair is tilted in unison to obtain different views of the breast. In all, each breast is generally imaged at least twice (two views per breast).

Additionally, the distance between the two detectors 12 and 14 may be changed to accommodate breasts with different sizes and to immobilize the breast for the duration of data acquisition, which may include applying light pressure to the breast. The distance between near faces of the two collimators 22 and 24 is registered automatically or manually. Although illustrated as a parallel hole collimators 22 and 24, different types of collimators as known in the art may be used, such as pinhole, fan-beam, cone-beam, diverging type collimators, and/or multi-bore per pixel collimators. An actual field of view (FOV) of each of the detectors 12 and 14 may be directly proportional to the size and shape of the respective imaging detector, or may be changed using collimation. In various embodiments, the detectors 12 and 14 may be formed of cadmium zinc telluride (CZT) tiles or alternatively any two-dimensional pixelated detector.

The MBI system 10 may also includes a motion controller unit 30 to control the movement and positioning of the gantry 16 and/or the detectors 12 and 14 with respect to each other to position the breast 20 within the FOVs of the imaging detectors 12 and 14 prior to acquiring an image of the breast 20. Optionally, the MBI system 10 may be operated manually by the user to reposition the detectors 12 and 14. Moreover, pressure sensors (not shown) may be used to assist the user in preventing from applying excessive force on the breast while positioning the breast between the detectors 12 and 14. The controller unit 30 includes a detector controller 32 and a gantry motor controller 34 that may be automatically commanded by a processing unit 36, manually controlled by an operator, or a combination thereof. The gantry motor controller 34 and the detector controller 32 may move the detectors 12 and 14 with respect to the breast 20 individually, in segments or simultaneously in a fixed relationship to one another. Alternatively, one or more collimators 22 and 24 may be moved relative to the detectors 12 and 14. The distance between the detectors 12 and 14 may be registered by the controller unit 30 and used by the processing unit 36 during data processing. In some embodiments, motion is manually detected by the operator and the controller unit 30 is replaced with scales or encoders for measuring the distance between the detectors 12 and 14, the detector orientation, and/or any immobilization force exerted by at least one detector 12 and/or 14 on the breast 20.

During operation, the breast 20 is positioned between the detectors 12 and 14 and at least one of the detectors 12 and/or 14 is translated to immobilize the breast 20 between the detectors 12 and 14. The detectors 12 and 14 are then used to acquire temporal image data of the breast 20, which may include one or more lesions, for example a breast cancer tumor, within the breast 20. The detectors 12 and 14 and the gantry 16 generally remain stationary after being initially positioned, and the temporal imaging data is acquired. The temporal imaging data may then be combined into a composite image that includes a plurality of two-dimensional (2D) images 46, wherein each 2D image 46 is acquired at a different point in time during the scan.

The MBI system 10 also includes a Data Acquisition System (DAS) 40 that receives analog and/or digital electrical signal data produced by the detectors 12 and 14 and decodes the data for subsequent processing in the processing unit 36. A data storage device 42 may be provided to store data from the DAS 40 or other types of data. For example, the data storage device 42 may store emission data 44 acquired from the detectors 12 and 14 during a scan of the breast 20. In various embodiments, the emission data 44 may be utilized generate a plurality of 2D images or frames 46 of the breast 20. Optionally, the emission data 44 may be stored as list mode data 48 of the breast 20 acquired during a previous scan, e.g. event-by-event data acquisition. In a "list-mode" acquisition, each detected photon is associated with: x, y, detector 12 or 14, and a "time stamp". The "time stamp" is the absolute time of the event, or time since the beginning of the acquisition. An input device 50 (e.g., user console with keyboard, mouse, etc.) also may be provided to receive user inputs and a display 52 may be provided to display images.

In various embodiments, the MBI system 10 also includes a motion detection and correction module 60 that is configured to implement various methods described herein. The module 60 may be implemented as a piece of hardware that is installed in, for example, the processing unit 36. Optionally, the module 60 may be implemented as a set of instructions that are installed on the processing unit 36. The set of instructions may be stand alone programs, may be incorporated as subroutines in an operating system installed on the processing unit 36, may be functions in an installed software package on the processing unit 36, and the like. It should be understood that the various embodiments are not limited to the arrangements and instrumentality shown in the drawings. For example, in some embodiments, the MBI system 10 may include a "viewing station" (not shown) that is used by the physician to evaluate the images. Thus, the motion detection and correction module 60 may be located at the "viewing station" which may be located remotely from the MBI system 10.

The set of instructions may include various commands that instruct the module 60 and/or the processing unit 36 as a processing machine to perform specific operations such as the methods and processes of the various embodiments described herein. The set of instructions may be in the form of a non-transitory computer readable medium. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
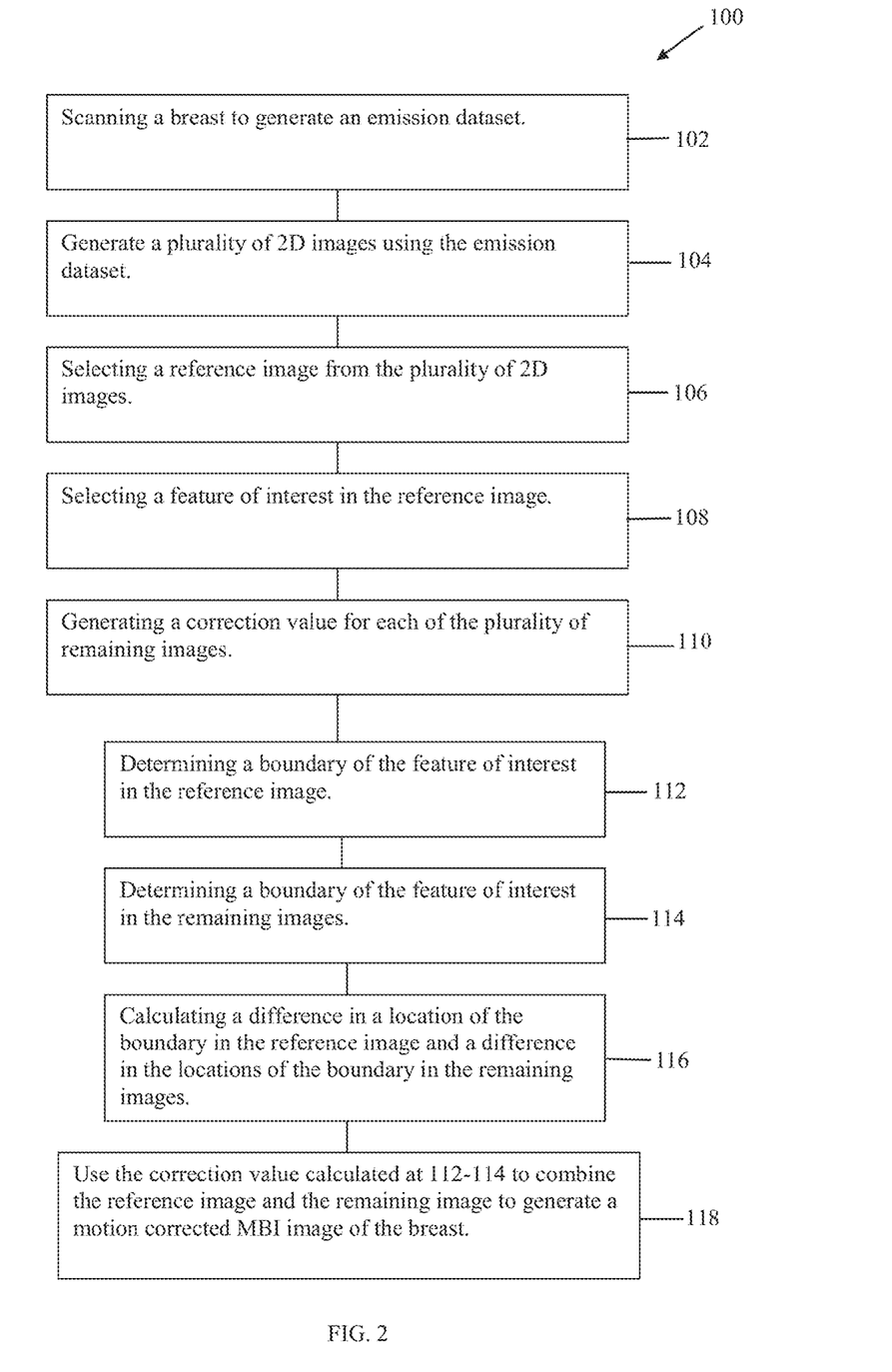
FIG. 2 is a method of detecting and correcting motion affected images in accordance with various embodiments.

FIG. 2 is a simplified block diagram of an exemplary method 100 that may be utilized to perform motion detection and correction of the images 46 and/or list mode data 48 described above. In various embodiments, the method 100 may be utilized to either automatically or manually select a portion of the breast 20 in a first or reference image in the set of 2D images 46 and then to register or align the non-reference images 46 with the reference image based on the selected portion. As used herein, the term "non-reference images" refers to each of the 2D images that are not designated as the reference image. Assuming that a set N of 2D images is generated, and a single referenced image is selected from the set of N 2D images. The non-reference 2D images form a set having N−1 images, e.g. the non-reference images. In the exemplary embodiment, the method 100 may be implemented using the processing unit 36 and/or the motion detection and correction module 60 (shown in FIG. 1). The method 100 may therefore be provided as a non-transitory computer-readable medium or media having instructions recorded thereon for directing the processing unit 36 and/or the motion detection and correction module 60 to perform an embodiment of the methods described herein. The medium or media may be any type of CD-ROM, DVD, floppy disk, hard disk, optical disk, flash RAM drive, or other type of computer-readable medium or a combination thereof.

Referring to FIG. 2, at 102 the patient's breast 20 is scanned to generate an emission dataset, such as the emission dataset 44 (shown in FIG. 1). In the exemplary embodiment, the emission dataset 44 may be acquired using the MBI system 10 (shown in FIG. 1). For example, the emission dataset 44 may be acquired by performing a scan of the breast 20 to produce the emission dataset 44. Optionally, the emission dataset 44 may be acquired from data collected during a previous scan of the breast 20, wherein the emission dataset 44 has been stored in a memory, such as the data storage device 42 (shown in FIG. 1). The emission dataset 44 may be stored in any format, such as a plurality of 2D images 46 or a list mode dataset 48, for example. The emission dataset 44 may be acquired during real-time scanning of the breast 20. For example, the methods described herein may be performed on emission data as the emission dataset 44 is received from the MBI system 10 during a real-time examination of the breast 20.

Figure 3:
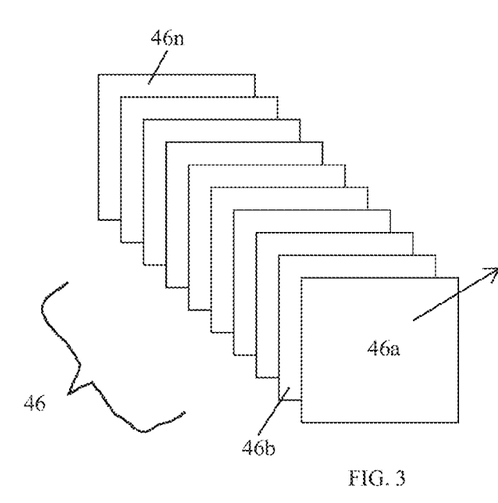
FIG. 3 is a simplified block diagram of a plurality of images that may be generated in accordance with various embodiments.

At 104, a plurality of 2D images, such as the 2D images 46 are generated using the emission dataset 44 acquired at 102. More specifically, and as shown in FIG. 3, assume that at 102 a length of the scan of the breast 20 is ten minutes. Moreover, assume that an operator desires to generate a 2D image using emission data acquired over a 1 minute period. Accordingly, in the exemplary embodiment, shown in FIG. 3, ten 2D images labeled 46a . . . 46n are generated. It should be realized that the breast 20 may be scanned for any length of desired time, and ten minutes is one such exemplary scan time. Moreover, it should be realized that a single 2D image may be generated using emission data acquired over any length of time. For example, assume again that the breast 20 is scanned for five minutes. Moreover, assume that each 2D image is generated using emission data acquired over a thirty second time period. In this example, fifteen 2D images 46 are generated at 104.

Figure 4:
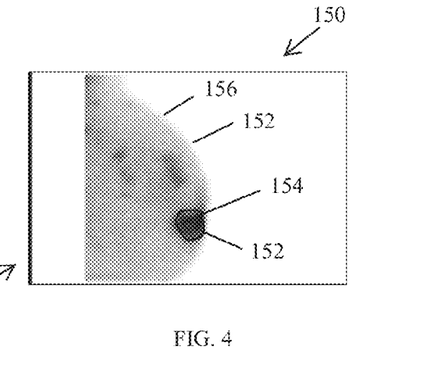
FIG. 4 is a two-dimensional image that may be generated in accordance with various embodiments.

Referring again to FIG. 2, method 100 further includes selecting at 106 a reference image 150 from the plurality of 2D images 46, for example, selecting the 2D image 46a shown in FIG. 3, as the reference image 150 shown in FIG. 4. In operation, the reference image 150 is used as a baseline image for aligning each of the non-reference images 46b . . . 46n with the reference image 150. More specifically, and as described in more detail below, the location or coordinates of a feature of interest in the reference image 150 are initially determined. The location or coordinates of the same feature of interest are then determined in each of the non-reference images 46b . . . 46n. The coordinates of the feature of interest in the non-reference images 46b . . . 46n may then be shifted, using a correction value, such that the feature of interest in the non-reference images 46b . . . 46n is at the same coordinates as the feature of interest in the reference image 150. More specifically, the non-reference images 46b . . . 46n are registered with respect to the reference image 150 based on the correction value, as described in more detail below. Accordingly, when the reference image 150 is combined with the non-reference images 46b . . . 46n to form a final 2D image, the feature of interest selected by the user is aligned in each of the 2D images such that the final 2D image has reduced blurring, etc. In various embodiments, any of the 2D images may be selected as the reference image 150. In the illustrated embodiment, the first 2D image 46a acquired during the scan of the breast 20 is selected as the reference image 150. However, it should be realized that any of the non-reference images 46b . . . 6n acquired during the scan of the breast 20 may be selected as the reference image 150.

Referring again to FIG. 2, at 108 a feature of interest 152 in the reference image 150 is selected. In various embodiments, the feature of interest 152 may be a tumor, lesion, or other physical feature 154 within the breast 20. In other embodiments, the feature of interest 152 may be an edge, surface or wall 156 of the breast 20. In operation, the feature of interest 152 selected in the reference image 150 is utilized to register or align the non-reference images 46a . . . 46n with the reference image 150, e.g. the 2D image 46a. For example, assume that upon reviewing the reference image 150, the user determines that two lesions are shown. The user may determine that a first lesion is of clinical importance while the second lesion is not of clinical importance. The two lesions may appear at first locations in the reference image 150 and at different locations in the non-reference images 46b ... 46n as the patient moves. The user may select, using the input device 50 for example the first lesion as the feature of interest 152 such that when the non-reference images 46b ... 46n are combined with the reference image 150, the feature of interest 152 is aligned in each of the images, and the resultant or final 2D image shows the feature of interest 152 having reduced blurring, etc, to enable the user to measure or otherwise quantify the lesion more accurately.

At 110 a correction value is calculated for each of the non-reference images 46b ... 46n based on a difference in a location of the feature of interest 152 in the reference image 150 and a location of the feature of interest 152 in the non-reference images 46b ... 46n. For example, the correction value may represent a set of X-Y coordinates that are used to align the feature of interest 152 in the non-reference images 46b ... 46n with the feature of interest 152 in the reference image 150. More specifically, the correction value may be a set of X-Y coordinates that represent a difference between the position of the feature of interest 152 in the non-reference images 46b ... 46n and the position of the feature of interest 152 in the reference image 150. The correction value may also represent a vector having a direction and a magnitude, wherein the direction indicates the direction along the X-axis and/or the Y axis the feature of interest 152 in the non-reference images 46b ... 46n should be moved to align the feature of interest 152 in the non-reference images 46b ... 46n with the feature of interest 152 in the reference image 150. The magnitude of the vector represents a quantity of movement in the along the X-axis and/or the Y axis to move the feature of interest 152 in the non-reference images 46b ... 46n to align the feature of interest 152 in the non-reference images 46b ... 46n with the feature of interest 152 in the reference image 150. The correction value is determined for each of the non-reference images 46b ... 46n. In various embodiments, to generate the correction value at 110, a boundary of the feature of interest 152 in the reference image 150 is determined at 112. Moreover, at 114 the boundary of the feature of interest 152 in the non-reference images 46b ... 46n is determined.

Figure 5A:
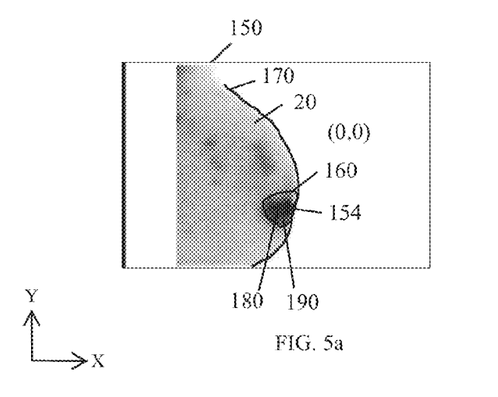
FIGS. 5A and 5B are two-dimensional images that may be generated in accordance with various embodiments.
Figure 5B:
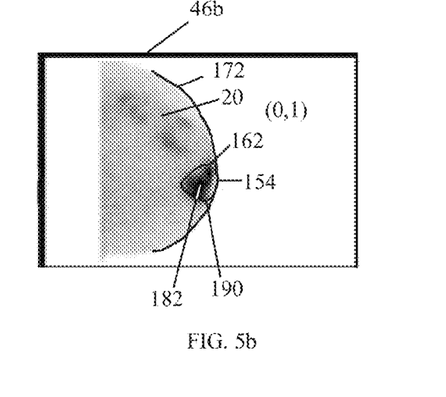

For example, FIG. 5A shows the reference image 150 wherein the lesion 154 is positioned at a first location. Moreover, FIG. 5B shows the 2D image 46b wherein the lesion 154 is positioned at a second location due to patient movement between the acquisition of the reference image 150 and the acquisition of the 2D image 46b. In various embodiments, at 112 a boundary 160 is calculated for the lesion 154 in the reference image 150 and at 114 a second boundary 162 is calculated for the lesion 154 shown in the 2D image 46b. It should be realized that the boundary 160 is substantially similar to the boundary 162, e.g. has the same size and shape. However, because the location of the lesion 154 in the reference image 150 is different than the location of the lesion 154 in the image 46b, due to patient motion, the location of the boundary 160 in the reference image 150 is different than the location of the boundary 162 in the image 46b. For example, as shown in FIG. 5A, assume that a center 190 of the lesion 154 is located at X,Y coordinates (0,0). Moreover, assume that the center 190 of the lesion 154 as shifted in FIG. 5B to X, Y coordinates (0,1). Thus, in the exemplary embodiment, the lesion 154 is the same in the X direction in both the reference image 150 and the image 46b. However, because of motion, the lesion 154 has shifted in the Y direction. Accordingly, the correction value calculated for the image 46b may be for example, (0,−1) to instruct the processing unit 36 to shift the image 46b by one pixel in the Y direction such that lesion 154 in image 46b is aligned with the lesion 154 in the reference image 150. Accordingly, when the image 46b is combined with the reference image 150, the feature of interest 152, e.g. the lesion 154 is aligned in all of the images. Similarly, a boundary is calculated for the other non-reference images 46c ... 46n to align the lesion 154 in the images 46c ... 46n with the lesion 154 in the reference image.

In various embodiments, the boundaries 160 and 162 may be calculated by a user manually drawing or virtually tracing on a screen the boundaries 160 and 162, respectively, that enclose the lesion 154 as shown in FIGS. 5A and 5B. The boundaries 160 and 162 may be drawn around the lesion 154 using the input device 50, for example. In other embodiments, the boundaries 160 and 162 may be calculated semi-automatically, wherein a user defines a center point within the lesion 154 and the processing unit 36 then defines the boundaries 160 and 162 based on the defined center point. For example, when the boundaries 160 and 162 are calculated semi-automatically, the user may position a center point 180 and a center point 182 on the lesion 154 in both the reference image 150 and the non-reference images 46b ... 46n, the processing unit 36 may then automatically calculate the boundaries 160 and 162. The boundaries 160 and 162 may also be generated automatically using the processing unit 36 and/or the motion detection and correction module 60. For example, the processing unit 36 may determine a pixel intensity vale for each pixel in the reference image 150 and the non-reference images 46b ... 46n. The processing unit 36 may then compare the pixel intensity values to known pixel intensity values of, for example, a known lesion. Based on the comparison, the processing unit 36 may automatically identify the lesion 154 and automatically draw a boundary around the lesion 154 as described above.

More specifically, the processing unit 36 generates the boundaries 160 and 162 using a principle, whereby it is generally assumed that various organs, tissue, fluid, and other anatomical features, surrounding the lesion 154 may be differentiated from the lesion 154 by determining an intensity value for each pixel in the reference image 150 and the 2D image 46b. Based on the intensity values of each of the pixels, the lesion 154 may be distinguished from the other anatomical features. Accordingly, the boundary 160 is calculated by automatically comparing the intensity value for each pixel in the reference image 160 to a predetermined intensity value, using for example, a thresholding process to identify the lesion 154 and generate the boundary 160 around the lesion 154. Automatic determination of the lesion may be done for example by calculating the average "non-air" intensity. The threshold may then be set to a predefined percentage (e.g. 20% or 50% above average). Optionally, a "histogram" of pixel values may be plotted, wherein the lowest (~"0") peak is air, the main peak="normal tissue", and the higher peak(s)= lesion(s). The threshold may be set at "valley" above the main peak. Similarly, the boundary 162 is calculated by automatically comparing the intensity value for each pixel in the 2D image 46b to a predetermined intensity value, using for example, a thresholding process to identify the lesion 154 and generate the boundary 162 around the lesion 154 in the 2D image 46b.

Similarly, the processing unit 36 may generates boundaries around the surface of the breast 20. For example, and referring again to FIGS. 5A and 5B, the processing unit 36 may generate a boundary 170 around a portion of the breast 20 in the reference image 150. Moreover, the processing unit 36 may generate a boundary 172 around a portion of the breast 20 of the 2D image 46b as shown in FIG. 5B. In various embodiments, the boundaries 170 and 172 are determined or calculated similar to the boundaries 160 and 162 described above. For example, and as described above it is generally assumed that breast tissue and the other physical features within the breast 20, such as for example the lesion 154, may be differentiated from the area surrounding the breast 20 which is air. Therefore intensity values of the pixels representing the breast 20 are different than the intensity values of the pixels surrounding the breast 20. Based on the intensity values of each of the pixels, the breast 20 may be distinguished from air surrounding the breast 20. Accordingly, the boundaries 170 and 172 are calculated by automatically comparing the intensity value for each pixel in the reference image 160 to a predetermined intensity value, using for example, a thresholding process to identify boundaries 170 and 172, respectively between the breast 20 and the air.

More specifically, to generate the boundaries 170 and 172, the method automatically compares the intensity value for each pixel in the reference image 150 to a predetermined intensity value, using for example, a thresholding process. In the exemplary embodiment, the predetermined intensity value may be a range of predetermined intensity values. The predetermined value range may be automatically set based on a priori information of the breast 20. Optionally, the predetermined range may be manually input by the operator. In one embodiment, if the intensity value of a pixel is within the predetermined range, the pixel is classified as belonging to the breast 20. Otherwise, the pixel is classified as not belonging to the air. It should be realized that other methods may be utilized to calculate the boundaries 170 and 172 of the breast 20.

Optionally, the processing unit 36 may determine the correction values based on the center points 180 themselves. For example, the processing unit 36 may compare the location of the center point 180 to each of the center points 182 in the non-reference images 46b . . . 46n to generate a plurality of correction values, wherein each correction value represents a difference in the location of the center point 180 and the center points 182 in the non-reference images 46b . . . 46n.

Accordingly, at 110 the correction value, in some embodiments, is calculated by determining a difference in a location, e.g. the boundary 160, of the feature of interest 152 in the reference image 150 and a location, e.g. the boundary 162, of the feature of interest 152 in the non-reference images 46b . . . 46n. Optionally, the correction value is generated using the center points 180 and 182 described above. More specifically, at the X-Y coordinates of the boundary 162 are compared to the baseline X-Y coordinates of the boundary 160 in the reference image 150 to calculate a difference in the location of the boundary 160 in the reference image 150 and each of the boundaries 162 calculated in the non-reference images 46b . . . 46n. The difference in the X-Y coordinates of the boundary 160 and the X-Y coordinates of the boundaries 162 in each of the non-reference images 46b . . . 46n are referred to herein as the correction values. It should be appreciated that a correction value is calculated for each of the non-reference images 46a . . . 46n to enable each of the non-reference images 46b . . . 46n to be aligned with the reference image 150.

Figure 6:
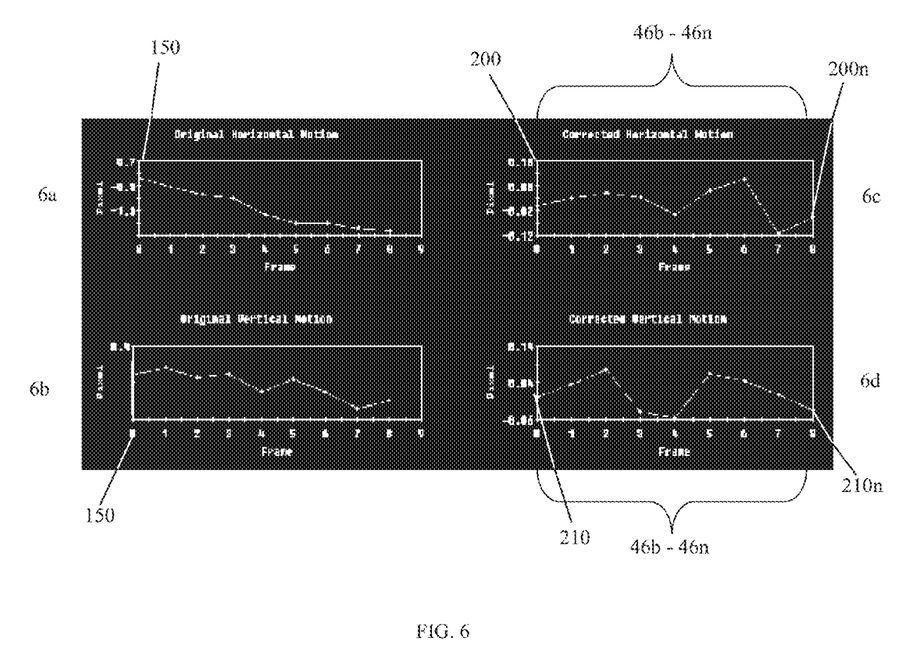
FIGS. 6A-6D are graphical illustrations of exemplary correction values that may be generated in accordance with various embodiments.

For example, FIGS. 6A-6D are a plurality of graphical illustrations showing exemplary the movement of the breast 20 during the image acquisition process and a plurality of correction values that may be generated using the various methods and systems described herein. In FIGS. 6A-6D, the x-axis represents the image number and the y-axis represents the location of the feature of interest 152. As shown in FIG. 6A, the left side of the graph shows the horizontal position of the feature of interest 152 in the reference image 150 denoted at position 0. Positions 1-9 on the x-axis show the horizontal position of the feature of interest 152 in the non-reference images 46b . . . 46n. Additionally, as shown in FIG. 6B, the left side of the graph shows the vertical position of the feature of interest 152 in the reference image 150 denoted at position 0. Positions 1-9 on the x axis show the vertical horizontal position of the feature of interest 152 in the non-reference images 46b . . . 46n.

FIG. 6C illustrates the positions 0-8 on the x-axis show the horizontal position of the feature of interest 152 after the correction is applied to align each of the non-reference images 46b . . . 46n to the reference image 150 in the horizontal direction. Additionally, FIG. 6D illustrates the positions 0-8 on the x-axis show the vertical position of the feature of interest 152 after the correction is applied to align each of the non-reference images 46b . . . 46n to the reference image 150 in the vertical direction. Accordingly, each of the points 200 . . . 200n represent correction values applied to each of the non-reference images 46b . . . 46n in the horizontal direction and each of the points 210 . . . 210n represent correction values applied to each of the non-reference images 46b . . . 46n in the vertical direction.

Referring again to FIG. 2, at 118 the correction value calculated at 110 is utilized to align the non-reference images 46b . . . 46n to the reference image 150 such that when the reference image 152 is combined with the non-reference images 46b . . . 46n, a single motion correction 2D image of the breast 20 is generated. It should therefore be realized that a correction value is calculated for each of the 2D images 46b . . . 46n. In the illustrated embodiment, because there are nine non-reference images 46b . . . 46n, at 110 nine correction values are calculated, one correction value for each of the non-reference images. Optionally, the correction analysis is performed in real time (during the acquisition). If the correction value is above a threshold value (e.g. 0.5 cm or 1 cm) for any of the images, the user is alerted to instruct the patient not to move. The entire imaging procedure may optionally repeated, or extended in time to ensure quality, or the correction analysis is performed immediately at the end of the imaging (while the patient is in the room). If the correction value is above a threshold value (e.g. 0.5 cm or 1 cm) for any of the images, the user is alerted to repeat the imaging.

Described herein are methods and systems to correct for distortions, such as motion related blurring or artifacts caused as a result of patient motion during an MBI scan of a patient's breast. The method and systems described herein therefore provide improved imaging (better contrast, lesion detectability) without adding additional hardware or other costly components to the MBI system. The methods and systems described herein facilitate reducing patient dosage which may be caused by longer scans that have higher potential of patient motion It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for motion correcting molecular breast imaging (MBI) images, said method comprising:
    obtaining a plurality of two-dimensional (2D) images during a scan of a breast using a MBI system, wherein the plurality of 2D images are acquired at different times during the scan and each include a feature of interest;
    selecting a reference image from the plurality of 2D images, the plurality of 2D images remaining correspond to a plurality of non-reference images;
    selecting the feature of interest in the reference image;
    determining a location of the feature of interest in the reference image;
    calculating correction values for each of the plurality of non-reference images, wherein the correction values are based on a difference in the location of the feature of interest in the reference image and a location of the feature of interest in each of the plurality of non-reference images; and
    combining the plurality of non-reference images with the reference image to form a motion correction 2D image based on the calculated correction values.

2. The method of claim 1, wherein said obtaining a plurality of two-dimensional (2D) images of a breast using a MBI system comprises:
    acquiring data from the MBI system in a list mode format; and
    creating a plurality of two-dimensional (2D) images from the acquired data in a list mode format, wherein each one of the two-dimensional (2D) images is generated from a sub-set of events in the data acquired from the MBI system in the list mode format.

3. The method of claim 1, wherein selecting a feature of interest comprises displaying the reference image on a display; and selecting at least one of a breast wall or a physical feature within the breast based on user inputs from an input device.

4. The method of claim 1, wherein calculating the correction values comprises:
    identifying a boundary of the feature of interest in the reference image based on a center point of the feature of interest;
    identifying a boundary of the feature of interest in each of the plurality of non-reference images; and
    calculating a shift between the boundary of the feature of interest in the reference image and the boundary of the feature of interest in the plurality of non-reference images.

5. The method of claim 1, wherein calculating the correction values comprises calculating a difference between a location of a boundary of the feature of interest in the reference image and a boundary of the feature of interest in the plurality of non-reference images, wherein the correction values are a set of X-Y coordinates.

6. The method of claim 1, wherein calculating the correction values comprises:
identifying a center point of the feature of interest in the reference image;
identifying a center point of the feature of interest in each of the plurality of non-reference images; and
calculating a shift between the center point of the feature of interest in the reference image and the center points of the feature of interest in the plurality of non-reference images.

7. The method of claim 1, wherein the MBI system includes two detectors, said method further comprising:
generating a first 2D image using emission data acquired from the first detector;
generating a second 2D image using emission data acquired from the second detector; and
combining the first and second 2D images to generate the reference image.

8. The method of claim 1, wherein the MBI system includes a pair of CZT detectors configured to immobilize the breast there between.

9. A molecular breast imaging (MBI) system comprising:
at least one detector having a plurality of pixels; and
a processing unit having one or more processors, the processing unit is coupled to the detector, the processing unit configured to
obtain a plurality of two-dimensional (2D) images during a scan of a breast using a MBI system, wherein the plurality of 2D image are acquired at different times during the scan and each include a feature of interest;
receive a user input selecting a reference image from the plurality of 2D images, the plurality of 2D images remaining correspond to a plurality of non-reference images;
receive a user input selecting the feature of interest in the reference image;
determine a location of the feature of interest in the reference image;
calculate a correction value for each of the plurality of non-reference images, where the correction values are based on a difference in the location of the feature of interest in the reference image and a location of the feature of interest in the plurality of non-reference images; and
combine the plurality of non-reference images with the reference image to form a motion correction 2D image based on the calculated correction values.

10. The MBI system of claim 9, further comprising a pair of CZT detectors configured to immobilize the breast there between.

11. The MBI system of claim 9, wherein the processing unit is further configured to:
acquire data from the MBI system in a list mode format; and
create a plurality of two-dimensional (2D) images from the acquired data in a list mode format, wherein each one of the two-dimensional (2D) images is generated from a sub-set of events in the data acquired from the MBI system in the list mode format.

12. The MBI system of claim 9, wherein the processing unit is further configured to:
identify a boundary of the feature of interest in the reference image based on a center point of the feature of interest;
identify a boundary of the feature of interest in each of the plurality of non-reference images; and
calculate a shift between the boundary of the feature of interest in the reference image and the boundaries of the feature of interest in the plurality of non-reference images.

13. The MBI system of claim 9, wherein the processing unit is further configured to calculate a difference between a location of a boundary of the feature of interest in the reference image and a boundary of the feature of interest in the plurality of non-reference images.

14. The MBI system of claim 9, wherein the processing unit is further configured to:
receive a user input identifying a center point of the feature of interest in the reference image;
automatically identify a center point of the feature of interest in each of the plurality of non-reference images; and
calculate a shift between the center point of the feature of interest in the reference image and the center points of the feature of interest in the plurality of non-reference images.

15. The MBI system of claim 9, wherein the processing unit is further configured to:
generate a first 2D image using emission data acquired from the first detector;
generate a second 2D image using emission data acquired from the second detector; and
combine the first and second 2D images to generate the reference image.

16. A non-transitory computer readable medium encoded with a program to instruct a processing unit to:
obtain a plurality of two-dimensional (2D) images during a scan of a breast using a MBI system, wherein the plurality of 2D images are acquired at different times during the scan and each include a feature of interest;
receive a user input selecting a reference image from the plurality of 2D images, the plurality of 2D images remaining correspond to a plurality of non-reference images;
receive a user input selecting the feature of interest in the reference image;
determine a location of the feature of interest in the reference image;
calculate correction values for each of the plurality of non-reference images based on a difference in a location of the feature of interest in the reference image and a location of the feature of interest in each of the plurality of non-reference images; and
combine the plurality non-reference images with the reference image to form a motion correction 2D image based on the calculated correction values.

17. The non-transitory computer readable medium of claim 16, further encoded with a program to instruct a processing unit to:
acquire data from the MBI system in a list mode format; and
create a plurality of two-dimensional (2D) images from the acquired data in a list mode format, wherein each one of the two-dimensional (2D) images is generated from a sub-set of events in the data acquired from the MBI system in the list mode format.

18. The non-transitory computer readable medium of claim 16, further encoded with a program to instruct a processing unit to:
identify a boundary of the feature of interest in the reference image based on a center point of the feature of interest;

identify a boundary of the feature of interest in each of the plurality of non-reference images; and calculate a shift between the boundary of the feature of interest in the reference image and the boundaries of the feature of interest in the plurality of non-reference images.

19. The non-transitory computer readable medium of claim 16, further encoded with a program to instruct a processing unit to calculate a difference between a location of a boundary of the feature of interest in the reference image and a boundary of the feature of interest in the plurality of non-reference images.

20. The non-transitory computer readable medium of claim 16, further encoded with a program to instruct a processing unit to:

receive a user input identifying a center point of the feature of interest in the reference image;

automatically identify a center point of the feature of interest in each of the plurality of non-reference images; and calculate a shift between the center point of the feature of interest in the reference image.

\* \* \* \* \*